United States Patent [19]

Hammond et al.

[11] Patent Number: 4,581,122
[45] Date of Patent: Apr. 8, 1986

[54] STATE OF CHARGE ANALYTICAL APPARATUS

[75] Inventors: Michael J. Hammond, Sterling Heights; Mark W. Arendell, Warren, both of Mich.

[73] Assignee: Energy Development Associates, Inc., Madison Heights, Mich.

[21] Appl. No.: 386,536

[22] Filed: Jun. 9, 1982

[51] Int. Cl.[4] .......................................... G01N 27/46
[52] U.S. Cl. ................................ 204/412; 204/1 T; 204/400; 429/17; 429/20; 429/91; 429/105; 429/199
[58] Field of Search ................. 204/400, 412; 429/17, 429/20, 91, 105, 199

[56] References Cited

U.S. PATENT DOCUMENTS

| | | | |
|---|---|---|---|
| 3,713,888 | 6/1970 | Symons | 136/6 |
| 3,809,578 | 5/1974 | Symons | 136/6 E |
| 3,881,958 | 5/1975 | Carr et al. | 136/86 B |
| 4,138,322 | 2/1979 | Barnes et al. | 204/412 |
| 4,143,212 | 3/1979 | Ueno et al. | 429/91 |
| 4,146,437 | 3/1979 | O'Keefe | 204/412 |
| 4,467,017 | 8/1984 | Jackson | 429/91 |

OTHER PUBLICATIONS

"Development of the Zinc-Chlorine Battery for Utility Applications" by Energy Development Associates, Apr. 1979, pp. A-1-A-13.

*Primary Examiner*—T. Tung
*Attorney, Agent, or Firm*—Harness, Dickey & Pierce

[57] ABSTRACT

An electrochemical apparatus for analyzing the zinc concentration in an aqueous zinc-halogen electrolyte is disclosed. The electrochemical apparatus includes a working electrode and an auxiliary electrode both in contact with the electrolyte to be analyzed, a reference electrode in contact with an aqueous zinc-halogen electrolyte of a predetermined concentration, and means for permitting the electrolyte to be analyzed to contact the electrolyte of predetermined concentration. The apparatus also includes circuit means for applying electrical power to the working and auxiliary electrodes for a first predetermined time period sufficient to deposit zinc metal onto the working electrode, and for measuring a potential difference across the reference and working electrodes indicative of the concentration of the electrolyte to be analyzed during a second predetermined time period. A suitable chamber means may also be provided for containing at least the portion of the electrolyte to be analyzed, with the working and auxiliary electrodes mounted in the chamber means such that they are in contact with the electrolyte within the chamber means. Similarly, vessel means may be provided for containing a supply of the electrolyte of a predetermined concentration, with the reference electrode and the vessel means associated such that the reference electrode is in contact with the electrolyte of a predetermined concentration. The vessel means is formed with liquid junction means for permitting the electrolyte of a predetermined concentration to contact the electrolyte to be analyzed within the chamber means. The analytical method according to the present invention includes the steps of applying electrical power to the working and auxiliary electrodes for a first predetermined time period sufficient to deposit zinc metal onto the working electrode, and measuring the potential difference across the reference and working electrodes during a second predetermined time period.

11 Claims, 6 Drawing Figures

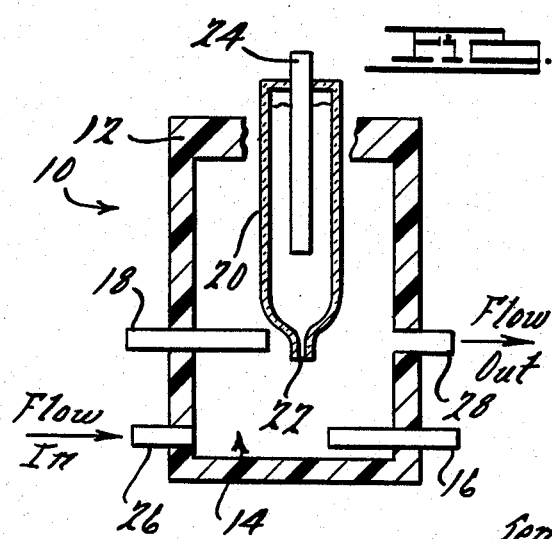
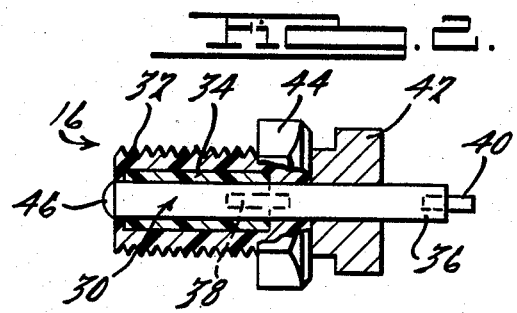
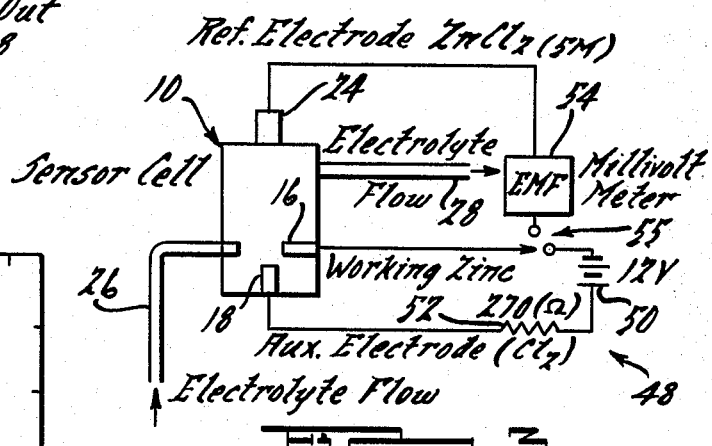
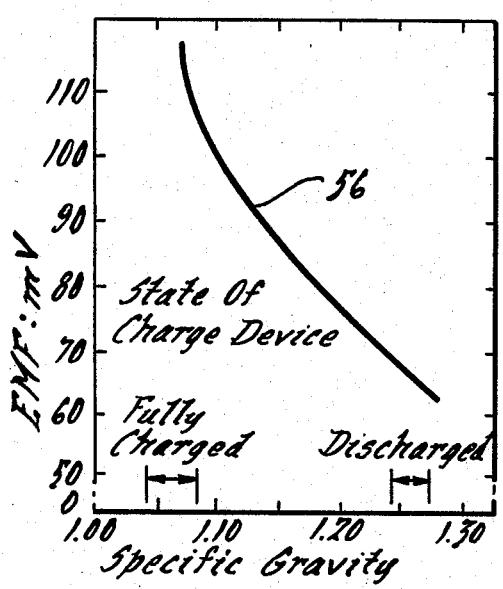
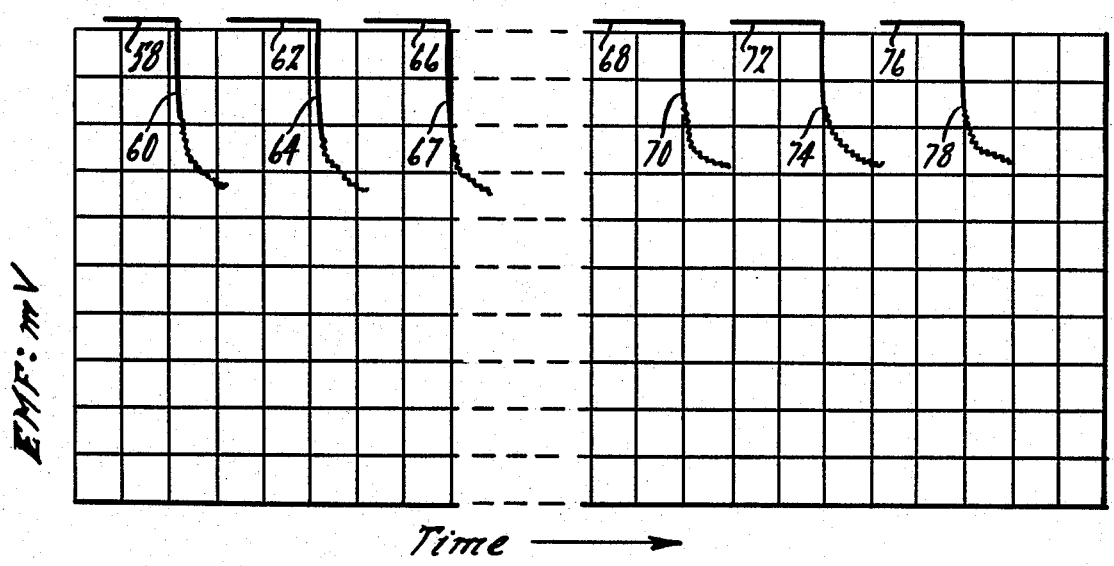

STATE OF CHARGE ANALYTICAL APPARATUS

BACKGROUND AND SUMMARY OF THE INVENTION

The present invention relates generally to aqueous electrolytes in electrochemical systems, and particularly to a method and apparatus for analyzing the zinc concentration of an aqueous zinc-halogen electrolyte in zinc-halogen secondary energy storage battery systems in order to determine the state of charge for these battery systems.

The secondary energy storage systems of the type referred to herein (e.g., a zinc-chloride battery system or other zinc-halogen battery system) generally are comprised of three basic components, namely an electrode stack section, an electrolyte circulation subsystem, and a store subsystem. The electrode stack section typically includes a plurality of cells connected together electrically in various series and parallel combinations to achieve a desired operating voltage and current at the battery terminals over a charge/discharge battery cycle. Each cell is comprised of a positive and negative electrode which are both in contact with an aqueous zinc-halogen electrolyte. The electrolyte circulation subsystem operates to circulate the zinc-halogen electrolyte from a reservoir through each of the cells in the electrode stack in order to replenish the zinc and halogen electrolyte components as they are oxidized or reduced in the cells during the battery cycle. In a closed, self-contained zinc-halogen battery system, the storage subsystem is used to contain the halogen gas or liquid which is liberated from the cells during the charging of the battery system for subsequent return to the cells during the discharging of the battery system. In the zinc-chloride battery system, chlorine gas is liberated from the positive electrodes of the cells and stored in the form of chlorine hydrate. Chlorine hydrate is a solid which is formed by the store subsystem in a process analogous to the process of freezing water where chlorine is included in the ice crystal.

With reference to the general operation of a zinc-chloride battery system, an electrolyte pump operates to circulate the aqueous zinc-chloride electrolyte from a reservoir to each of the positive "chlorine" electrodes in the electrode stack. These chlorine electrodes are typically made of porous graphite, and the electrolyte passes through the pores of the chlorine electrodes into a space between the chlorine electrodes and the opposing negative or "zinc" electrodes. The electrolyte then flows up between the opposing electrodes or otherwise out of the cells in the electrode stack and back to the electrolyte reservoir or sump.

During the charging of the zinc-chloride battery system, zinc metal is deposited on the zinc electrode substrates and chlorine gas is liberated or generated at the chlorine electrode. The chlorine gas is collected in a suitable conduit, and then mixed with a chilled liquid to form chlorine hydrate. A gas pump is typically employed to draw the chlorine gas from the electrode stack and mix it with the chilled liquid, (i.e., generally either zinc-chloride electrolyte or water). The chlorine hydrate is then deposited in a store container until the battery system is to be discharged.

During the discharging of the zinc-chloride battery system, the chlorine hydrate is decomposed by permitting temperature to increase, such as by circulating a warm liquid through the store container. The chlorine gas thereby recovered is returned to the electrode stack via the electrolyte circulation subsystem, where it is reduced at the chlorine electrodes. Simultaneously, the zinc metal is dissolved off of the zinc electrode substrates, and power is available at the battery terminals.

Further discussion of the structure and operation of zinc-chloride battery systems may be found in the following commonly assigned patents: Symons U.S. Pat. No. 3,713,888 entitled "Process For Electrical Energy Using Solid Halogen Hydrates"; Symons U.S. Pat. No. 3,809,578 entitled "Process For Forming And Storing Halogen Hydrate In A Battery"; Carr et al U.S. Pat. No. 3,881,958 entitled "Mass Flow Rate Control Of Chlorine Content Of Electrolyte For High Energy Density Battery"; Carr U.S. Pat. No. 4,100,332 entitled "Comb Type Bipolar Electrode Elements And Battery Stack Thereof". Such systems are also described in published reports prepared by the assignee herein, such as "Development of the Zinc-Chloride Battery for Utility Applications," Interim Report EM-1417, May 1980, and "Development of the Zinc-Chloride Battery for Utility Applications," Interim Report EM-1051, April 1979, both prepared for the Electric Power Research Institute, Palo Alto, Calif. The specific teachings of the aforementioned cited references are incorporated herein by reference.

Over the course of the zinc-chloride battery charge/discharge cycle, the concentration of the electrolyte varies as a result of the electrochemical reactions occurring at the electrodes in the cells of the electrode stack. At the beginning of charge, the concentration of zinc-chloride in the aqueous electrolyte may typically be 2.0 Molar. As the charging portion of the cycle progresses, the electrolyte concentration will gradually decrease with the depletion of zinc and chloride ions from the electrolyte. When the battery system is fully charged, the electrolyte concentration will typically be reduced to 0.5 Molar. Then, as the battery system is discharged, the electrolyte concentration will gradually swing upwardly and return to the original 2.0 Molar concentration when the battery system is completely or fully discharged.

The present invention is directed to a method and apparatus for analyzing or determining the zinc concentration in the electrolyte of zinc chloride and other zinc-halogen battery systems to determine the state of charge of these battery systems. While in many other battery systems resort must be had to detecting sensitive changes in the overall voltage of the battery to determine the state of charge, it will be appreciated that the variation in the electrolyte concentration described above for the zinc-chloride battery system provides for an accurate and reliable means for determining the state of charge. In the laboratory, the electrolyte concentration may be readily determined by employing a hydrometer and calibrating the specific gravity to the Molar concentration of the electrolyte. However, this technique is not practical for a commercial battery system.

Accordingly, it is a principle object of the present invention to provide an apparatus and method of analyzing the zinc concentration in an aqueous zinc-halogen electrolyte which may be employed in closed self-contained secondary energy storage battery system in order to determine the state of charge for the battery system.

It is a more specific object of the present invention to provide an electrochemical apparatus and method for analyzing the zinc concentration in an aqueous zinc-chloride electrolyte which is accurate and reliable even when the electrolyte to be analyzed is saturated with dissolved chlorine.

It is another object of the present invention to provide an electrochemical apparatus and method of analyzing the zinc concentration in an aqueous zinc-chloride electrolyte where a flow of the electrolyte to be analyzed is provided through the apparatus.

It is a further object of the present invention to provide an electrochemical apparatus and method of analyzing the zinc concentration in an aqueous zinc-chloride electrolyte which is operable from a low voltage d.c. power source, such as a conventional portable battery.

It is an additional object of the present invention to provide an electrochemical apparatus and method of analyzing the zinc concentration in an aqueous zinc-chloride electrolyte of a zinc-chloride battery system which will not contaminate or otherwise introduce foreign matter into the battery system.

To achieve the foregoing objects, the present invention provides an electrochemical apparatus for analyzing or determining the zinc concentration in an aqueous zinc-halogen electrolyte which includes a working electrode and an auxiliary electrode both in contact with the electrolyte to be analyzed, a reference electrode in contact with an aqueous zinc-halogen electrolyte of a predetermined concentration, and means for permitting the electrolyte to be analyzed to contact the electrolyte of predetermined concentration. The apparatus also includes circuit means for applying electrical power to the working and auxiliary electrodes for a first predetermined time period sufficient to deposit zinc metal onto the working electrode, and for measuring a potential difference across the reference and working electrodes indicative of the concentration of the electrolyte to be analyzed during a second predetermined time period. A suitable chamber means may also be provided for containing at least the portion of the electrolyte to be analyzed, with the working and auxiliary electrodes mounted in the chamber means such that they are in contact with the electrolyte within the chamber means. Similarly, vessel means may be provided for containing a supply of the electrolyte of a predetermined concentration, with the reference electrode and the vessel means associated such that the reference electrode is in contact with the electrolyte of a predetermined concentration. The vessel means is formed with liquid junction means for permitting the electrolyte of a predetermined concentration to contact the electrolyte to be analyzed within the chamber means. The predetermined concentration of the electrolyte within the vessel means may be any suitable concentration which provides for stable and consistent results. The analytical method according to the present invention includes the steps of applying electrical power to the working and auxiliary electrodes for a first predetermined time period sufficient to deposit zinc metal onto the working electrode, and measuring the potential difference across the reference and working electrodes during a second predetermined time period.

Additional advantages and features of the present invention will become apparent from a reading of the detailed description of the preferred embodiment which makes reference to the following set of drawings in which:

BRIEF DESCRIPTION OF THE DRAWINGS

FIG. 1 is a simplified plan elevation view, partially in cross-section, of a sensor cell adapted to be employed in an electrochemical apparatus for analyzing the concentration of an aqueous zinc-halogen electrolyte in accordance with the present invention.

FIG. 2 is a plan elevation view, partially in cross-section, of a working electrode assembly for the sensor cell apparatus illustrated in FIG. 1.

FIG. 3 is a simplified schematic diagram of an electrochemical apparatus according to the present invention employing the sensor cell illustrated in FIG. 1, and particularly featuring the circuit means for the apparatus.

FIG. 4 is a graph of the potential difference (EMF) measured by the apparatus illustrated in FIG. 3 as a function of the specific gravity of the electrolyte over a charge/discharge battery cycle.

FIG. 5 is a graph illustrating several potential difference (EMF) measurements taken with respect to time in accordance with the method of the present invention.

DETAILED DESCRIPTION OF THE PREFERRED EMBODIMENT

Figure 6:
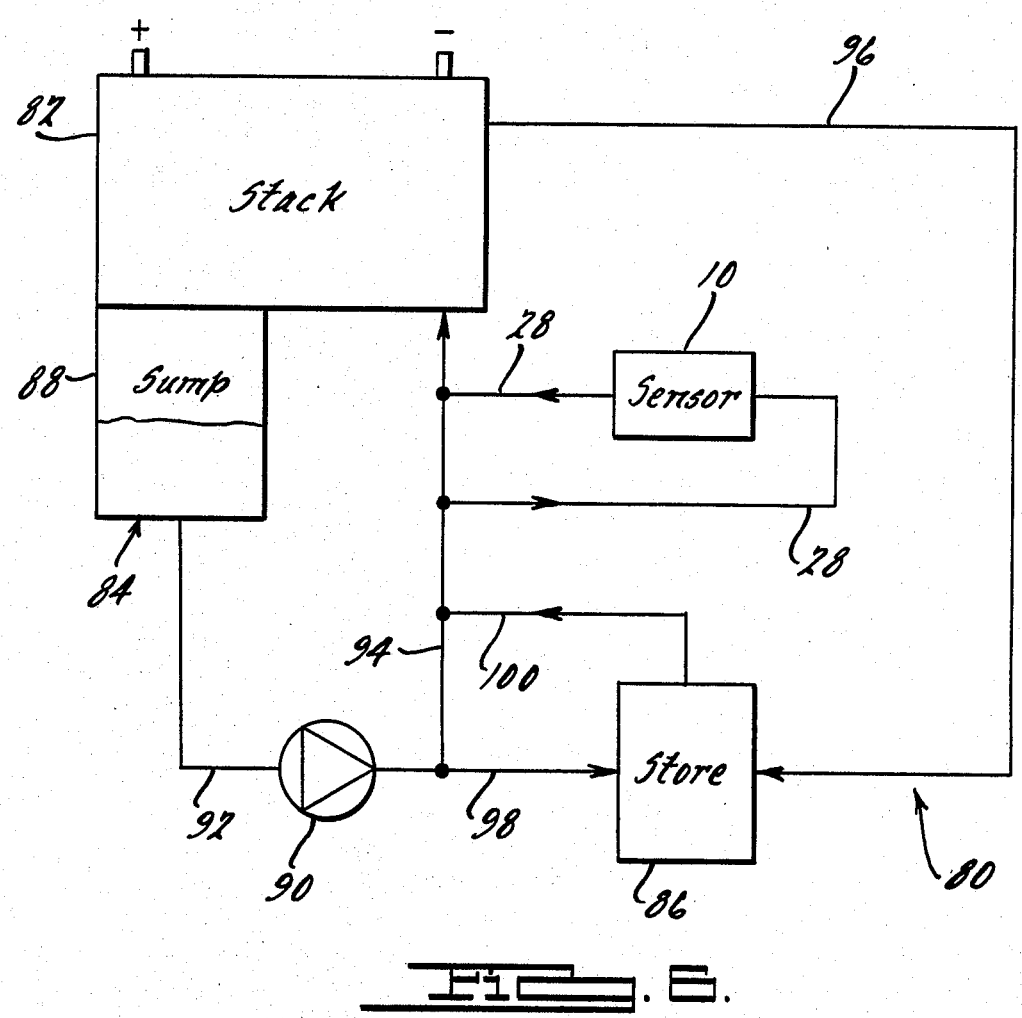
FIG. 6 is a block diagram of a zinc-chloride battery system employing the electrochemical apparatus illustrated in FIG. 3.

Referring to FIG. 1, a sensor cell 10 for an electrochemical apparatus according to the present invention is shown. The sensor cell 10 includes a housing or container 12 which forms a cell chamber 14 for containing at least a portion of the zinc-halogen electrolyte to be analyzed. A working electrode assembly 16 is mounted to the housing 12 and extends into the chamber 14 such that the working electrode is in contact with the electrolyte to be analyzed within the chamber. Similarly, an auxiliary electrode assembly 18 is mounted to the housing 12 and extends into the chamber 14 such that the auxiliary electrode is in contact with the electrolyte to be analyzed. A vessel 20 is also provided, and extends through a suitable aperature in the top of the housing 20 into the chamber 14. The vessel 20 is adapted to contain an aqueous zinc-halogen electrolyte of a predetermined concentration, and is formed with a liquid junction 22 which permits the electrolyte of a predetermined concentration within the vessel 20 to contact the electrolyte to be analyzed within the chamber 14. A reference electrode 24 extends into the vessel 20 such that the reference electrode is in contact with the electrolyte of a predetermined concentration.

The sensor cell 10 may also be provided with a conduit 26 for permitting electrolyte to flow into the chamber 14 and a conduit 28 for permitting electrolyte to flow out of the chamber. While it may be preferred for the electrolyte contained in the chamber 14 to be in a static dechlorinated condition, it has been found that the sensor cell 10 operates satisfactorily even when the electrolyte contained in the chamber 14 is under dynamic conditions. Thus, when the sensor cell 10 is employed in a zinc-halogen battery system, the electrolyte concentration within the chamber 14 will be permitted to change with the changing concentration of the battery electrolyte via the flow of electrolyte through conduits 26 and 28.

With respect to materials which may be used to construct the sensor cell 10, it should be noted that both the housing 12 and the vessel 20 may be constructed from any suitable electrically non-conductive material which is also chemically resistant or inert to the electrolyte and other chemical entities with which they will come into contact. Thus, the housing 12 and the vessel 20 may be constructed from such materials as General Tire and Rubber Corp., Boltron polyvinylchloride (4008-2124), DuPont teflon (tetrafluorinated ethylene), Kynar (polyvinyldynene fluoride), or any of the other appropriate materials described in section 33 of the Development Of The Zinc Chloride Battery For Utility Applications Report, April 1979, identified above. Additionally, it may be noted that the vessel 20 may also be constructed from a conventional glass enclosure used in commercial PH meter electrodes assemblies. The liquid junction 22 of the vessel 20 may be comprised of a capiliary passageway through the walls of the vessel, a porous glass frit, or other suitable porous medium which will permit the electrolyte within the vessel to contact the electrolyte contained in the chamber 14. As to the conduits 26 and 28, a suitably chemically resistant or inert plastic, such as teflon, may be employed.

Referring to FIG. 2, an enlarged plan elevation view, partially in cross-section, of the working electrode assembly 16 is shown. The working electrode assembly 16 generally comprises a graphite reference electrode 30 contained in a conventional ¼" Teflon fitting 32, and a layer 34 of an insulating material extending along substantially the entire axial length of the electrode 30. The graphite working electrode 30 is connected to a metal rod 36 via axial screw 38, and an axial screw 40 is mounted to the opposite end of the metal rod 36 to provide a convenient means for making an electrical connection. A metal collar 42 is coaxially disposed over the metal rod 36 in order to provide a fluid tight seal with a cap 44 of the fitting 32. Both the metal rod 36 and the metal sleeve 42, as well as the axial screws 38 and 40, may be constructed from any suitable electrically conductive material which is also chemically resistant or inert to the electrolyte and other chemical entities with which they will come into contact, such as titanium or tantalum. The insulating layer 34 may be comprised of any of the materials identified above for the housing 12 and vessel 20, including heat shrinkable kynar tubing. The purpose of the insulating layer 34 is to shield the graphite working electrode 30 so that only a tip portion 46 of the electrode is exposed to the electrolyte contained in the chamber 14. As will be more fully discussed below, this shielding of the graphite working electrode 30 operates in combination with the position of the conduit 26 to direct the flow of electrolyte past the tip portion 46 of the working electrode.

With respect to the auxiliary electrode assembly 18 and the reference electrode assembly 24, both of these assemblies may be constructed similarly to the construction illustrated for the working electrode assembly 16. However, it should be noted that since there is no advantage to shielding these electrodes, an insulating layer corresponding to the insulating layer 34 of the electrode assembly 16 need not be provided for the auxiliary and reference electrode assemblies. As to the auxiliary electrode itself, this electrode may be constructed from porous or dense graphite, or other suitable metal such as titanium or tantalum. With respect to the reference electrode, it is preferred that a commercially pure grade of zinc metal be employed. Although other materials such as calomel or silver chloride may be employable for the reference elecrtrode, the voltaic potentials of these materials greatly exceeds the voltaic changes due to variations in the electrolyte concentration. Accordingly, the use of these materials is considered to increase the difficulty of achieving an accurate electrolyte concentration analysis. Additionally, the use of calomel and silver chloride electrodes or the like also introduce the possibility of contaminating the electrolyte being analyzed with mercury and silver respectively. As will be appreciated by those skilled in the art, the presence of the liquid junction 22 will cause a very gradual exchange in the electrolytes contained in the chamber 14 and the vessel 20. Indeed, it may be necessary in some applications to replenish the supply of electrolyte contained in the vessel 20 over extended periods of time. Accordingly, it is possible for the materials used to construct the reference electrode to be transferred to the electrolyte within the chamber 14 through the liquid junction 22. However, where zinc metal is employed as the reference electrode no contamination is possible as the electrolyte being analyzed is itself comprised at least in part of zinc.

Referring to FIG. 3, a simplified schematic diagram of an electrochemical apparatus 48 for analyzing or determining the zinc concentration in an aqueous zinc-halogen electrolyte in accordance with the present invention is shown. The apparatus 48 generally comprises the sensor cell 10, and circuit means interconnecting the working electrode 30 with the auxiliary and reference electrodes. The circuit means is used for applying electrical power to the working and auxiliary electrodes for a first predetermined time period sufficient to deposit zinc metal onto the tip portion 46 of the working electrode, and for measuring a potential difference across the reference and working electrodes indicative of the concentration of the electrolyte to be analyzed during a second predetermined time period. The circuit means includes charging means for applying electrical power to the working and auxiliary electrodes, meter means for measuring a potential difference across the reference and working electrodes, and switch means for controlling the application of electrical power to the working and auxiliary electrodes from the charging means.

In one form of the present invention, the charging means is a source of d.c. electrical power 50 having its positive terminal electrically connected to the auxiliary electrode. As shown in FIG. 3, the power source 50 is a twelve volt battery, and a resistor 52 is connected electrically in series with the battery and the auxiliary electrode. The voltage of the power source 50 and the resistance of the resistor 52 combined to provide a voltage across the working and auxiliary electrodes during the first predetermined time period which will place these electrodes into a "charging" condition (i.e., approximately 2.5 volts). In this condition, zinc metal will be deposited onto the tip portion 46 of the working electrode, and a halogen (such as chlorine gas) will be liberated or generated at the auxiliary electrode. Accordingly, it should be appreciated that during the first predetermined time period the working and auxiliary electrodes combined to form a single zinc-halogen cell.

In one form of the present invention, the meter means comprises a millivolt meter 54 having one terminal electrically connected to the reference electrode and the other terminal connected to the switch means 55. The switch means 55, as illustrated in FIG. 3, may simply be a single throw double pole manually actuated switch 55 which is operable to connect the working electrode to the negative terminal of the power source 50 during the first predetermined time period and to connect the working electrode to the millivolt meter 54 during the second predetermined time period. It should be understood that the particular switch means described above is intended to be exemplary only, and that other suitable switch means may be employed in the appropriate application. For example, it may be desirable for the switch means to comprise an electronic controlled conduction device and the necessary timing circuitry to provide for automatic operation of the apparatus 48. Additionally, it should be noted that the particular choice of charging means described above is also intended to be exemplary only, and serves to illustrate that the apparatus 48 may operate from a conventional automotive battery as may be desirable when the zinc-halogen battery system is employed as the power source in an electric vehicle. Alternatively, it may be desirable for the apparatus 48 to derive its operating power from the zinc-halogen battery itself during the discharge of the battery system.

The principal of operation for the electrochemical apparatus 48 is based upon the Nernst equation $$EMF = E° - (RT/NF) \text{ Log } Q,$$

where "E°" is the standard cell emf, "R" is the gas constant (1.987 cal/°K.), "T" is the absolute temperature, "N" is the number of moles of electrons transferred in the reaction (i.e., the number of faradays), "F" is the faraday constant (23,060 cal/V), and "Q" is the reaction quotient. The reaction quotient "Q" is a fraction derived from the activities of the dissolved substances and gases employed in the cell, and it is assumed that the activity of a substance in solution is given by the Molar concentration of the substance. With zinc metal deposited onto the graphite substrate of the working electrode 30, the working electrode temporarily assumes the characteristics of a zinc electrode and combines with the reference electrode to form a concentration cell. In such a concentration cell, the reaction quotient "Q" becomes a fraction of the Molar concentration of the electrolyte in the chamber 14 divided by the Molar concentration of the electrolyte contained in the vessel 20, as follows:

$$Q = [Zn_B{}^{2+}]/[Zn_R{}^{2+}],$$

where the subscript "B" indicates that the numerator in the equation represents the Molar concentration of the battery electrolyte to be analyzed (that is, the electrolyte contained in the chamber 14), and the subscript "R" indicates that the denominator in the equation represents the Molar concentration of the reference electrolyte (that is, the electrolyte of a predetermined concentration contained in the vessel 20).

The above-identified concentration cell is formed during the second predetermined time period of operation where the reference and working electrodes are connected electrically through the millivolt meter 54, and may be characterized as follows:

$$Zn | Zn_B{}^{2+} (0.5-2.0M) | | Zn_R{}^{2+} (5.0M) | Zn,$$

where the term (0.5–2.0M) represents a typical electrolyte concentration swing from 0.5 to 2.0 Molar for a zinc-halogen battery, and the term (5.0M) represents a predetermined electrolyte concentration of 5.0 Molar for the electrolyte contained in the vessel 20.

From the foregoing, it should be appreciated that the voltaic potential difference (EMF) measured across the reference and working electrodes by the millivolt meter 54 should follow the equation:

$$EMF = E° - \frac{RT}{NF} \text{ Log } \frac{[Zn_B2+]}{[Zn_R2+]}$$

However, since the same electrode material (i.e. zinc) is used for both the reference and working electrodes during the second predetermined time period, the standard cell emf "E°" for the concentration cell is zero. Accordingly, the above equation may be reduced to:

$$EMF = -\frac{RT}{NF} \text{ Log } \frac{[Zn_B2+]}{[Zn_R2+]}$$

Referring to FIG. 4, a typical response of the electrochemical apparatus 48 as a function of the specific gravity for the electrolyte contained in the chamber 14 is illustrated. More specifically, FIG. 4 is a graph of the potential difference (EMF) measured by the apparatus 48 as a function of the electrolyte specific gravity over a charge/discharge battery cycle. It should be noted that the curve 56 illustrated represents an average of experimental data taken over several charge/discharge cycles of a zinc-chloride battery cell. The predetermined concentration for the electrolyte in the vessel 20 was 5.0 Molar, and electrolyte was permitted to flow through the chamber 14 at a rate between 10 to 20 (cc/minute). Additionally, the cell electrolyte temperature was permitted to vary from 20 to 30 (°c.) during charge and from 30 to 40 (°c.) during discharge. As illustrated in FIG. 4, the voltaic potential difference (EMF) across the working and reference electrodes varies between approximately 110 millivolts to 65 millivolts over a complete charge/discharge cycle, and this variation is generally logrythmic in nature. While the response of the apparatus 48 is illustrated with respect to the specific gravity of the electrolyte, it should be appreciated that the apparatus may also be calibrated with respect to the Molar concentration of the electrolyte or the state of charge. The term "state of charge" as used herein refers to both charge and discharge, and represents the amount of useable energy presently stored in a battery relative to the total energy storage capacity of the battery.

Referring to FIG. 5, a graph illustrating several potential difference (EMF) measurements taken with respect to time in accordance with the method of the present invention is shown. This graph represents a typical output of a strip chart recorder connected as the millivolt meter 54. Each square of the graph represents a centimeter. The strip chart recorder was calibrated to 10 millivolts per centimeter along the EMF axis and adjusted to record one centimeter per minute along the time axis.

FIG. 5 illustrates the record of six individual measurements employing the apparatus 48 to analyze the zinc concentration in a zinc-chloride electrolyte during the charging of a zinc-chloride battery cell. A curve portion 58 represents the floating potential of the reference electrode during the first predetermined time period when the working and auxiliary electrodes are in a charging condition; whereas, a curve portion 60 represents the potential difference across the working and reference electrodes during the second predetermined time period. It is important to note that the potential difference measured drops very rapidly at the beginning of the second predetermined time period, but then becomes a gradual drift after approximately thirty seconds. This gradual drift initiates a third predetermined time period in which the voltaic difference measured is indicative of the concentration of the electrolyte being analyzed.

In one method according to the present invention, both the second and third predetermined time periods end simultaneously at the beginning of the next measurement, as illustrated in FIG. 5 by a curve portion 62. However, if a single measurement were permitted to continue, the voltaic potential difference across the reference and working electrodes would continue to gradually drift downwardly and eventually reach zero. This zero potential point would be reached when the tip portion 46 of the working electrode 30 has been completely stripped of the zinc metal deposited thereon during the first predetermined time period. Accordingly, the second predetermined time period may extend until the potential difference across the reference and working electrodes is zero. With respect to the third predetermined time period, this period commences generally 30 seconds after the first predetermined time period has ended (or the second predetermined time period has begun) and may extend for one or more minutes in duration as long as the gradual drift continues. While it is preferred that the third predetermined time period has a duration between thirty seconds to two minutes from the beginning of the second predetermined time period, it will be appreciated that these times may be varied in the appropriate application. For example, in FIG. 5 the curve portion 58 indicates that the first predetermined time period was approximately two minutes in duration and the second predetermined time period was permitted to extend for approximately one minute from the ending of the first predetermined time period. However, if the first predetermined time period was permitted to extend for three minutes in duration, it may be desirable to extend the duration of the second predetermined time period.

FIG. 5 also serves to illustrate the reliability and accuracy of the electrochemical apparatus 48 as the measurements taken during related time periods are nearly identical. The first three measurements, as represented by curve portions 58–67, were taken over a period of approximately nine minutes with very close results (as indicated by the shape of the curve portions during the second predetermined time period). Similarly, the second three measurements, as represented by curve portions 68–78, were also taken over a period approximately nine minutes with very close results. However, the broken lines in the graph between the two sets of measurements indicate that some period of time has elapsed before the second set of measurements were taken. Indeed, approximately one hour was permitted to elapse between these two sets of measurements. It should be noted that the period of gradual drift for the first set of measurements is somewhat lower voltaically with respect to the gradual drift for the second set of measurements. Accordingly, these measurements indicate that the voltaic potential difference between the reference and working electrodes has increased several millivolts during this one hour period of charging a zinc chloride battery cell, as would be expected from the curve 56 in FIG. 4. To enhance the reliability and accuracy of the apparatus 48, it is preferred that a voltaic measurement be taken or recorded at a specific time during the third predetermined time period as a reference point or time. This reference time, for example, may be forty seconds from the beginning of the second predetermined time period. With such a reference time, the first three measurements of FIG. 5 would indicate a voltaic potential difference of approximately 69 millivolts, while the second set of measurements would indicate a voltaic potential difference of approximately 75 millivolts.

The shape of the curves shown in FIG. 5 during the third predetermined time periods indicates that the zinc metal deposited upon the tip portion 46 of the working electrode 30 is being dissolved off of the electrode substrate at a significant rate. This rapid dissolution of zinc metal is the result of a chemical corrosion process due to the presence of chlorine in the electrolyte of the zinc chloride cell. During both the charging and discharging of a zinc chloride battery cell, dissolved chlorine will be present in the battery electrolyte, and during discharge the electrolyte may in fact become saturated with dissolved chlorine. Since the chemical dissolution of zinc is the controlling reaction at the working electrode, it would not be expected that the apparatus 48 would respond to changes in the electrolyte concentration (as illustrated in FIGS. 4 and 5). Rather, it would be expected for the apparatus 48 to respond to the mass transfer of dissolved chlorine in the electrolyte to the working electrode 30. This effect is even compounded when an electrolyte flow is introduced through the chamber 14 of the sensor cell 10. The flow of electrolyte through the sensor cell 10 via the conduits 26 and 28 will, of course, increase the mass transfer of chlorine to the working electrode 30, and should exascerbate the interference to the operation of the apparatus due to the active dissolution of zinc by the dissolved chlorine. Although the presence of dissolved chlorine in the electrolyte was found to depress the EMF by several millivolts with respect to dechlorinated electrolyte, this depression was found to become essentially constant once the chlorine concentration exceeded a minimal level. Additionally, it was found that deviations in the flow rate of approximately thirty percent did not materially effect the accuracy of the measurements made. Accordingly, it is believed that the response of the electrochemical apparatus 48 to changes in the electrolyte concentration being analyzed is a surprising result under the conditions outlined above. It should also be noted that while the working electrode 30 and the conduit 26 are positioned to direct the flow of electrolyte at the tip portion 46 of the working electrode and thereby enhance the mass transfer of dissolved chlorine to the working electrode, this geometry also assures that the electrolyte concentration being analyzed will be the most representative of the electrolyte concentration in the battery.

As to the predetermined concentration of the electrolyte contained within the vessel 20, any suitable electrolyte concentration may be employed which provides for stable and consistent results. In one form of the present invention this electrolyte concentration is sufficiently greater than the maximum concentration of the electrolyte to be analyzed so as to provide for a potential difference across the reference and working electrodes during the second predetermined time period regardless of a variation in the zinc concentration. In this embodiment, the predetermined concentration of the electrolyte is at least twice the magnitude of the maximum concentration of the electrolyte to be analyzed. Thus, with respect to the electrolyte contained in a zinc chloride battery system, the predetermined concentration of the electrolyte in the vessel 20 would be at least 4.0 Molar. In addition to the reasons outlined above for the predetermined electrolyte concentration, a relatively high concentration with respect to the electrolyte concentration being analyzed will also make the zinc reference electrode more resistant to dissolution, as the electrolyte solution will already be concentrated with zinc chloride. Furthermore, any dissolution of the zinc reference electrode which may occur will not appreciably affect the results obtained, because an initially high concentration of zinc in the electrolyte will minimize the relative shift in electrolyte concentration. However, other suitable electrolyte concentrations may be employed in the appropriate application, such as a concentration substantially equal to the maximum zinc concentration of the electrolyte to be analyzed.

Referring to FIG. 6, a block diagram of a zinc chloride battery system 80 employing the electrochemical apparatus 48 is illustrated. The zinc chloride battery system 80 includes a electrode stack section 82, an electrolyte circulation subsystem 84, and a store subsystem 86. The electrolyte circulation subsystem 84 includes a sump or reservoir 88 for containing a supply of zinc chloride electrolyte, an electrolyte pump 90, and conveying conduits 92 and 94 for circulating the electrolyte from sump 88 to the stack section 82. A conduit 96 is provided to permit the chlorine gas generated in the electrode stack section 82 during the charging of the battery system to be transferred to the store subsystem 86 where chloride hydrate is formed. The liquid used to form the chlorine hydrate is provided by the battery electrolyte itself via a conduit 98, and any excess electrolyte filtered from the hydrate is returned to the electrolyte circulation subsystem via a conduit 100. Additionally, the conduit 100 also serves to return chlorine to the electrode stack section 82 via the electrolyte circulation subsystem during the discharging of the battery.

The sensor cell 10 is shown to be connected to the electrolyte circulation conduit 94 via the conduits 26 and 28 in the zinc chloride battery system 80. However, it should be appreciated that the sensor cell 10 may be connected to the electrolyte circulation subsystem 84 at other suitable locations, such as along the conduit 92. Additionally, it should be noted that in one form of the present invention the housing 12 may comprise the walls of the conduit 94 itself in the appropriate application. However, for this in-line location it may be desirable to place a baffle or other obstruction around the tip portion 46 of the working electrode 30 in order to control the electrolyte flow rate past the working electrode. It should also be noted that regardless of the relative location of the sensor cell 10, the fluid pressure in the chamber 14 should not be permitted to significantly exceed the fluid pressure within the vessel 20, as a significant difference in pressure may cause electrolyte to be forced through the liquid junction 22 into the vessel 20, thereby altering the results obtained.

It will be appreciated that the above disclosed embodiment is well calculated to achieve the aforementioned objects of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope and spirit of the appended claims.

What is claimed is:

1. An electrochemical apparatus for analyzing the zinc concentration in an aqueous zinc-halide electrolyte, comprising:
    a working electrode in contact with said electrolyte to be analyzed;
    an auxiliary electrode in contact with said electrolyte to be analyzed;
    a reference electrode in contact with an aqueous zinc-halide electrolyte of a predetermined concentration;
    means for permitting said electrolyte to be analyzed to contact said electrolyte of a predetermined concentration, said predetermined concentration being greater than the maximum zinc concentration of said electrolyte to be analyzed;
    conveying means for permitting a flow of said electrolyte to be analyzed past said working electrode, dissolved halogen being present in said electrolyte to be analyzed; and
    circuit means for applying electrical power to said working and auxiliary electrodes for a first predetermined time period sufficient to deposit zinc metal onto said working electrode, and for measuring a potential difference across said reference and working electrodes indicative of the zinc concentration in said electrolyte to be analyzed during a second predetermined time period, said circuit means including a source of d.c. electrical power having its positive terminal electrically connected to said auxiliary electrode, a meter having one terminal electrically connected to said reference electrode, and a switch operable to connect said working electrode to the negative terminal of said source of d.c. electrical power during said first predetermined time period and to connect said working electrode to the other terminal of said meter during said second predetermined time period.

2. The electrochemical apparatus according to claim 1, wherein only a tip portion of said working electrode is in contact with said electrolyte to be analyzed.

3. The electrochemical apparatus according to claim 2 wherein said reference electrode is comprised of zinc metal, and said working and auxiliary electrodes are comprised of graphite.

4. The electrochemical apparatus according to claim 3, wherein said predetermined concentration of said electrolyte is at least twice the magnitude of the maximum concentration of said electrolyte to be analyzed.

5. An electrochemical apparatus for analyzing the zinc concentration in an aqueous zinc-chloride electrolyte, comprising:
    a graphite rod working electrode having only its tip in contact with said electrolyte to be analyzed;
    a graphite auxiliary electrode in contact with said electrolyte to be analyzed;
    a zinc reference electrode in contact with an aqueous zinc-chloride electrolyte of a predetermined concentration;
    means for permitting said electrolyte to be analyzed to contact said electrolyte of a predetermined concentration, said predetermined concentration being greater than the maximum zinc concentration of said electrolyte to be analyzed;

conveying means for permitting a flow of said electrolyte to be analyzed between said working and auxiliary electrodes and past said working electrode, dissolved chlorine being present in said electrolyte to be analyzed; and circuit means for applying electrical power to said working and auxiliary electrodes for a first predetermined time period sufficient to deposit zinc metal onto said working electrode, and for measuring a potential difference across said reference and working electrodes indicative of the zinc concentration in said electrolyte to be analyzed during a second predetermined time period.

6. An electrochemical apparatus for analyzing the zinc concentration in an aqueous zinc-chloride electrolyte, comprising:

chamber means for containing at least a portion of said electrolyte to be analyzed;

vessel means for containing an aqueous zinc-chloride electrolyte of a predetermined concentration, said vessel means being at least partially disposed within said chamber means and being formed with a liquid junction means for permitting said electrolyte of a predetermined concentration to contact said electrolyte to be analyzed, said predetermined concentration being greater than the maximum zinc concentration of said electrolyte to be analyzed;

a reference electrode in contact with said electrolyte within said vessel means;

a working electrode in contact with said electrolyte within said chamber means;

an auxiliary electrode in contact with said electrolyte within said chamber means; and circuit means for applying electrical power to said working and auxiliary electrodes for a first predetermined time period sufficient to deposit zinc metal onto said working electrode, and for measuring a potential difference across said reference and working electrodes indicative of the zinc concentration in said electrode to be analyzed during a second predetermined time period.

7. In a zinc-chloride battery system having a plurality of cells forming an electrode stack, means for circulating an aqueous zinc-chloride electrolyte through said cells in said electrode stack, and store means for forming and storing chlorine hydrate from the chlorine gas liberated from said electrode stack during the charging of said battery system, an electrochemical apparatus for analyzing the zinc concentration in said electrolyte, comprising:

a working electrode in contact with said electrolyte associated with said circulating means;

an auxiliary electrode in contact with said electrolyte associated with said circulating means;

a reference electrode in contact with an aqueous zinc-chloride electrolyte of a predetermined concentration, said predetermined concentration being greater than the maximum zinc concentration of said electrolyte to be analyzed; means for permitting contact between said electrolyte in contact with the reference electrode and said electrolyte to be analyzed; and circuit means for applying electrical power to said working and auxiliary electrodes for a first predetermined time period sufficient to deposit zinc metal onto said working electrode, and for measuring a potential difference across said reference and working electrodes indicative of the zinc concentration in said electrolyte to be analyzed during a second predetermined time period, said first predetermined time period being significantly less than the time required to charge said zinc-chloride battery system.

8. The electrochemical apparatus according to claim 7 wherein dissolved chlorine is present in said electrolyte to be analyzed.

9. The electrochemical apparatus according to claim 8, including conveying means for permitting a flow of said electrolyte to be analyzed past said working electrode.

10. The electrochemical apparatus according to claim 9, wherein said circuit means includes charging means for applying electrical power to said working and auxiliary electrodes during said first predetermined time period, meter means for measuring a potential difference across said reference and working electrodes, and switch means for controlling the application of electrical power to said working and auxiliary electrodes from said charging means.

11. The electrochemical apparatus according to claim 10, wherein said predetermined concentration of said electrolyte is at least twice the magnitude of the maximum concentration of said electrolyte to be analyzed.

* * * * *